United States Patent [19]

Schneider et al.

[11] Patent Number: 5,343,857
[45] Date of Patent: Sep. 6, 1994

[54] RESPIRATORY ACCESSORY ACCESS PORT AND ADAPTOR THEREFORE

[75] Inventors: James Schneider; Kok-Hiong Kee, both of St. Louis, Mo.

[73] Assignee: Sherwood Medical Company, St. Louis, Mo.

[21] Appl. No.: 98,013

[22] Filed: Jul. 27, 1993

Related U.S. Application Data

[63] Continuation of Ser. No. 873,470, Apr. 24, 1992, abandoned.

[51] Int. Cl.⁵ .............................................. A61M 16/20
[52] U.S. Cl. ........................... 128/202.27; 128/207.14; 128/912; 128/200.23; 128/205.13; 128/207.16
[58] Field of Search ............... 604/171, 172, 247, 167, 604/169; 128/911, 912, 200.23, 202.27, 203.12, 200.22, 205.13, 207.14, 207.16, DIG. 26; 285/330, 331, 332, 332.1

[56] References Cited

U.S. PATENT DOCUMENTS

| | | | |
|---|---|---|---|
| 1,588,336 | 6/1926 | Richmond | 285/331 X |
| 1,952,451 | 3/1934 | Mitchell | 285/331 X |
| 3,202,442 | 8/1965 | Abbey | 285/331 X |
| 3,825,001 | 7/1974 | Bennet et al. | 128/214.4 |
| 3,991,762 | 11/1976 | Radford | 128/276 |
| 4,213,716 | 7/1980 | Carson et al. | 400/235.1 |
| 4,240,417 | 12/1980 | Holever | 128/203.12 |
| 4,346,702 | 8/1982 | Kubota | 128/207.14 |
| 4,351,328 | 9/1982 | Bodai | 128/202.16 |
| 4,351,619 | 9/1982 | Duke et al. | 400/208 |
| 4,426,062 | 1/1984 | Bowrom | 251/7 |
| 4,475,548 | 10/1984 | Muto | 128/207.14 |
| 4,510,933 | 4/1985 | Wendt | 128/207.14 |
| 4,523,868 | 6/1985 | Shaowick | 400/208 |
| 4,552,473 | 11/1985 | Paulak | 400/208 |
| 4,621,633 | 11/1986 | Nowacki et al. | 128/204.18 |
| 4,691,702 | 9/1987 | Chantzis | 128/207.16 |
| 4,696,296 | 9/1987 | Palmer | 128/207.16 |
| 4,747,711 | 5/1988 | Motta et al. | 400/208 |
| 4,751,924 | 6/1988 | Hammerschmidt et al. | 128/207.15 |
| 4,781,702 | 11/1988 | Herrli | 604/244 |
| 4,796,615 | 1/1989 | Bullock et al. | 128/202.27 |
| 4,805,611 | 2/1989 | Hodgkins | 128/207.14 |
| 4,825,859 | 5/1989 | Lambert | 128/202.16 |
| 4,834,710 | 5/1989 | Fleck | 604/171 |
| 4,836,199 | 6/1989 | Palmer | 128/207.16 |
| 4,850,350 | 7/1989 | Jackson | 128/207.16 |

(List continued on next page.)

FOREIGN PATENT DOCUMENTS

| | | | |
|---|---|---|---|
| 417265 | 1/1967 | Switzerland | 285/331 |
| 2029703 | 3/1980 | United Kingdom | 123/911 |

*Primary Examiner*—Edgar S. Burr
*Assistant Examiner*—Eric P. Raciti
*Attorney, Agent, or Firm*—Andrew J. Beck; Montgomery W. Smith; Gene B. Kartchner

[57] ABSTRACT

An endotracheal respiration system which includes a respirator manifold with a port for attachment and detachment of an accessory device thereto without interruption of continuous respiratory support of the patient. A particular embodiment includes a suctioning system for removal of fluids from a patient's lungs during respiratory support. The manifold of the respiration system includes an accessory access port which has a normally closed valve therein which remains closed regardless of the pressure changes within the manifold. However, the normally closed valve is positioned in the port such that placement of a specially designed male adaptor located on the suctioning device forces the normally closed valve to an open position, thus allowing passage of a suction catheter through the manifold into the patient. Removal of the male adaptor of the suctioning device allows the normally closed valve to return to its closed position, thus allowing continued operation of the respirator even when no accessory device is present in the accessory device access port. The male adaptor includes a housing which is specially adapted to be securable within the valve in the access port of the manifold so as to substantially inhibit pressure loss from the manifold while simultaneously forcing the valve to an open position.

9 Claims, 2 Drawing Sheets

U.S. PATENT DOCUMENTS

| | | | |
|---|---|---|---|
| 4,857,062 | 8/1989 | Russell | 604/256 |
| 4,938,210 | 7/1990 | Shene | 128/203.12 |
| 4,951,661 | 8/1990 | Sladek | 128/202.27 |
| 4,967,743 | 11/1990 | Lambert | 128/202.16 |
| 5,009,391 | 4/1991 | Steigerwald | 251/149.1 |
| 5,025,806 | 6/1991 | Palmer et al. | 128/203.12 |
| 5,029,580 | 7/1991 | Radford et al. | 128/207.14 |
| 5,053,014 | 10/1991 | Van Heugten | 604/167 |
| 5,057,093 | 10/1991 | Clegg | 604/283 |
| 5,065,754 | 11/1991 | Jensen | 128/200.26 |
| 5,073,164 | 12/1991 | Hollister et al. | 604/43 |
| 5,078,131 | 1/1992 | Foley | 128/203.15 |
| 5,083,561 | 1/1992 | Russo | 128/207.16 |
| 5,088,486 | 2/1992 | Jinotti | 128/207.14 |
| 5,114,254 | 5/1992 | Sato et al. | 400/207 |
| 5,134,996 | 8/1992 | Bell | 128/207.14 |
| 5,140,983 | 8/1992 | Jinotti | 128/207.14 |
| 5,158,569 | 10/1992 | Strickland | 604/283 |

RESPIRATORY ACCESSORY ACCESS PORT AND ADAPTOR THEREFORE

This is a continuation of copending application(s) Ser. No. 07/873,470 filed on Apr. 24, 1992, now abandoned.

BACKGROUND OF THE INVENTION

1. Field of the Invention

This invention relates generally to apparatus used in conjunction with respiration systems. More specifically, the present invention relates to a method and apparatus for attaching accessory devices to a respiration system. Even more specifically, the present invention relates to the attachment and detachment of accessory devices to a respirator manifold of a respiratory system without interrupting or inhibiting the continuous respiration assistance being given to a patient by the respiration system.

2. Prior Art

Respiratory systems used for the ventilation of critically ill patients are now commonly used in medical facilities. Typically, a prior art respiratory system includes a tracheal tube, positioned either directly, or through the nose or mouth, into the trachea of a patient, a manifold connected to the tracheal tube at one port position thereof, a source of breathable gas connected at a second port thereof, and a third port for allowing exhausted gas to exit the manifold. The purpose of the respiration system is to assist the patient in maintaining adequate blood oxygenation levels without over taxing the patient's heart and lungs.

While a patient is attached to a respiration system, it is periodically necessary to remove fluid from the patient's trachea or lungs. In the past, it has been necessary to disconnect the respirator system, either by removing the manifold, or by opening a port thereof, and inserting a small diameter suction tube down the tracheal tube and into the patient's trachea and lungs. The fluid was then suctioned from the patient and the suction catheter was removed and the respirator system reassembled. Because of the necessary interruption in respiratory support, a patient's blood oxygen often dropped to an unacceptably low level during the suctioning procedure, even when other previously known breathing assisting efforts were simultaneously provided.

One solution to the above problem, which is generally exemplary of the prior art, is shown in U.S. Pat. No. 5,073,164 by Hollister et al. in which the respirator manifold includes a fourth port thereon which is adapted to receive a connector of the suctioning device. The suctioning device positions a suction catheter within the manifold without substantial manifold pressure loss. The suction device includes an envelope which is sealed around the suction catheter in order to prevent contamination of the suction catheter surface which is intended to be inserted into the patient's trachea and lungs. Although this type of respirator manifold and suctioning device connection allows continuous respiratory support of the patient during suctioning of fluid from the patient's trachea and lungs, there nevertheless remain several drawbacks associated with its use. For example, removal of the suctioning device from the manifold, such as for the purpose of replacing the suctioning device or attaching another accessory to the manifold, e.g. a manual resuscitation bag or a metered dose inhaler, cannot be accomplished without loosing manifold pressure and compromising the integrity of the respiration system. Thus, respiratory support of the patient must be stopped whenever the suctioning device is removed from the fourth port of the manifold.

U.S. Pat. No. 4,351,328 to Bodai attempts to solve this problem by forming a fourth opening in the respiratory manifold which is blocked by a pre-punctured resilient seal through which a suction catheter can be passed without substantially affecting the integrity of the system, i.e., without substantial gas exchange or pressure loss between the interior of the manifold and the atmosphere. The Bodai device, although allowing entry and removal of a suction catheter in a respiratory manifold during continuous respiratory support of a patient, nevertheless fails to completely resolve the existing problem in the prior art. Specifically, the pre-punctured resilient material in the port allows only for the insertion of a suction catheter therethrough, and fails to accommodate a suctioning device which includes a collapsible envelope which surrounds and seals the catheter against contamination of exterior surfaces thereof. Further, there is no design consideration for the attachment of other accessory devices, such as a manual resuscitation bag or a metered dose inhaler, which are often necessary for use in the care of a patient.

Also, the system described by Bodai tends to cause mucous and other fluids from the patient's lungs and trachea to collect in the manifold as it is wiped from the prepunctured resilient seal when the suction catheter is removed therefrom. Because of this design problem, it is often necessary to replace the manifold of the respiration system from time to time on a regular basis.

There therefore exists a need in the art for a respiration system which includes a respiratory manifold which allows simple attachment and detachment of accessory devices during continuous patient respiratory support without substantial pressure loss from the system and without substantial collection of body fluids in the manifold.

OBJECTS AND SUMMARY OF THE INVENTION

A principle object of the present invention is to provide a patient respiration system which allows access thereto of accessory devices, such as a suction catheter system, without interruption of continuous patient respiratory support.

Another object of the present invention is to provide a respiration system which allows access of accessory devices thereto through a manifold port which is normally closed against the atmosphere which will open upon attachment of the accessory device and automatically reclose upon detachment thereof.

A further object of the present invention is to provide a respiration system having a manifold which includes an accessory device access port with a normally closed valve therein, and a male adaptor formed as part of the accessory device which is designed to be capable of sealing against the port and opening, the normally closed valve allowing interchangeable use of accessory devices within the manifold while maintaining manifold pressure integrity.

These and other objects of the present invention are realized in a presently preferred embodiment thereof, described by way of example and not necessarily by way of limitation, which provides for interchangeable use of accessory devices with a manifold of a respiration system during respiratory support of a patient, without comprising the integrity of the system by destroying the seal between the manifold interior and the atmosphere. The invention includes a respiration system manifold formed with an accessory device access port which includes a normally closed valve therein. The valve maintains the pressure differential between the atmosphere and the interior of the manifold regardless of manifold pressure fluctuations. The invention also includes a male adaptor formed to fit within the accessory device access port and to sealingly engage therewith. Positioning the male adaptor into the access port forces the normally closed valve to an open position. The access port and adaptor may include a detent and stop-type locking arrangement for locking the adaptor within the port against inadvertent withdraw thereof during use.

The male adaptor may be formed as part of any one of a number of common respiration system accessories, such as a suction catheter system, a metered dose inhaler, a manual resuscitation bag, bronchoscope or the like.

In the presently shown preferred embodiment of the invention, the male adaptor is part of a suction catheter system, and the adaptor may be modified to include a seal through which a suction catheter may be inserted for extension through the manifold into the patient's trachea and lungs. The adaptor may also be modified to include a fluid port to allow passage of fluids into the adaptor for the purpose of cleaning the suction catheter and the adaptor interior after use.

These and other objects and advantages of the present invention will become apparent from the following more detailed description, when taken in conjunction with the accompany drawings, in which like elements are identified with like numerals throughout.

DETAILED DESCRIPTION OF THE PREFERRED EMBODIMENTS

Figure 5:
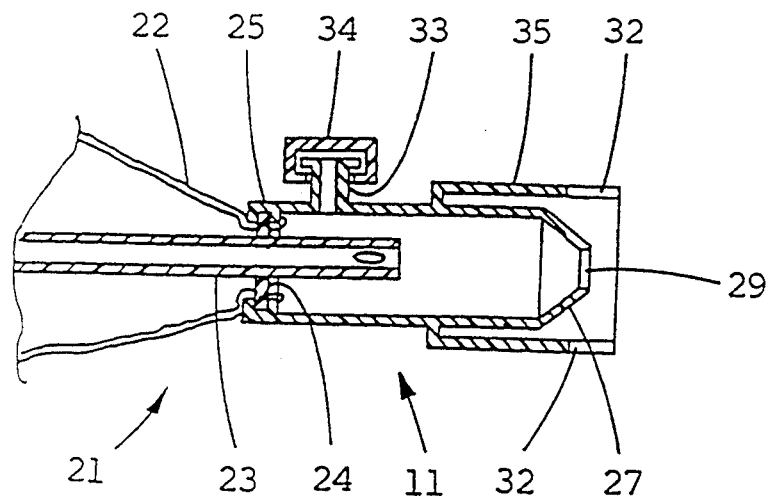
FIG. 5 is a cross-sectional view of a second preferred embodiment of the male adaptor formed in accordance with the principles of the present invention.

As shown in the exemplary drawings for the purposes of illustration, an embodiment of a respiration system manifold made in accordance with the principles of the present invention, referred to generally by the reference numeral 10, is provided for interchangeable access of respiration system accessory devices. Also is shown an embodiment of a male adaptor, referred to generally by the reference numeral 11, which is formed as part of a suction catheter system, and is provided for air-tight attachment to the manifold 10.

Figure 1:
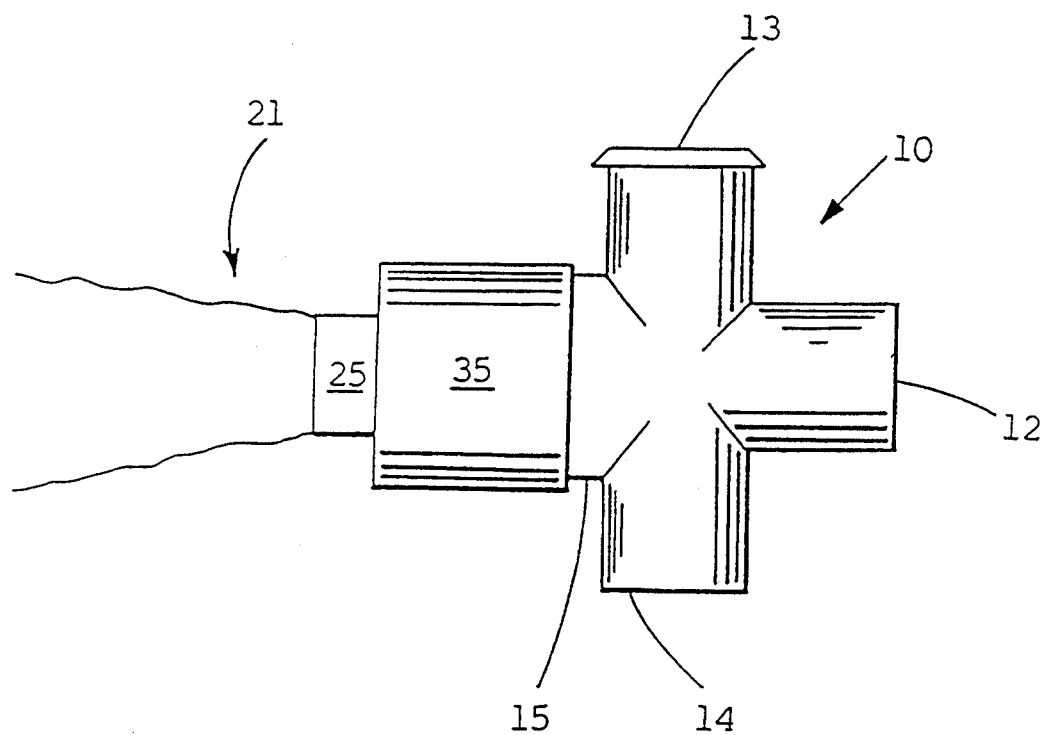
FIG. 1 shows a manifold of an aspiration system which has been modified to include an accessory device access port formed in accordance with the principles of the present invention, and including a male adaptor of an accessory device as also formed in accordance with the principles of the present invention inserted therein for use.

More specifically, as shown in FIG. 1, the respirator manifold 10 of the present invention includes a plurality of access ports which facilitate its connection to a ventilator circuit of the respiration system and to the patient. The manifold 10 is attached to a patient for fluid flow communication with the patient's lungs by the connection of the patient attachment port 12 to the connector of an endotracheal tube assembly (not shown) which has been previously positioned in the trachea of a patient by any one of several well known procedures.

Ventilator circuit connection ports 13 and 14 of the manifold 10 are designed for right or left side connection to flexible breathing hoses from the respiration system (not shown) in a well known manner, such as through a "Y" site connector. The ventilator circuit provides a high oxygen content gas mixture to the patient through one hose, and receives expelled air from the patient's lungs through the opposite hose. The ventilator circuit further commonly includes various valves, regulators and the like associated with the hoses attached to the manifold 10 to effect respiration of the patient. The manifold 10, and hoses attached thereto at the ventilator circuit connection port 13 or 14, are generally made of disposable plastic material and are generally intended to be used by only one patient and then discarded.

When attached to the patient, the entire respiratory system is designed to isolate the patient's lungs from the atmosphere and allow pressurized force ventilation of a gas mixture of a high oxygen content from the respirator into the patient's lungs. Further, common respirators employ a positive end expiratory pressure (PEEP) within the respirator manifold 10 and the patient's lungs at all times during exhalation. This technique is commonly used because of its benefit of requiring a minimum concentration of oxygen to be supplied to the patient for maintaining a proper blood oxygenation level. The PEEP procedure keeps a large number of lung alveoli of the patient open at all times during respirator support, thus increasing the effective lung area subject to ventilation.

Prevailing respiratory support techniques including PEEP, have made it very disadvantageous to interrupt respiratory support to the patient by opening the manifold to the atmosphere, (or detaching hoses from the manifold). Therefore, the attachment of accessory devices such as a closed system suction catheter or the like for necessary medical procedures has had to be avoided because of the loss of isolation of the respiratory system from the atmosphere during these procedures, and the immediate loss of effective lung surface area due to alveoli collapse. Further, when such procedures have taken an extended period of time to perform, blood oxygen levels have often dropped to inadequate levels, and caused over exertion of the patient's lungs and heart in order to return the blood oxygenation level to normal. Also, disassembly and reassembly of the respiratory system for procedures with prior art accessory devices can also be very time consuming for the medical worker.

The present invention resolves the problems associated with loss of isolation of the respiratory system from the atmosphere when these various accessory devices must be used to perform necessary medical procedures during respiratory support.

Figure 2:
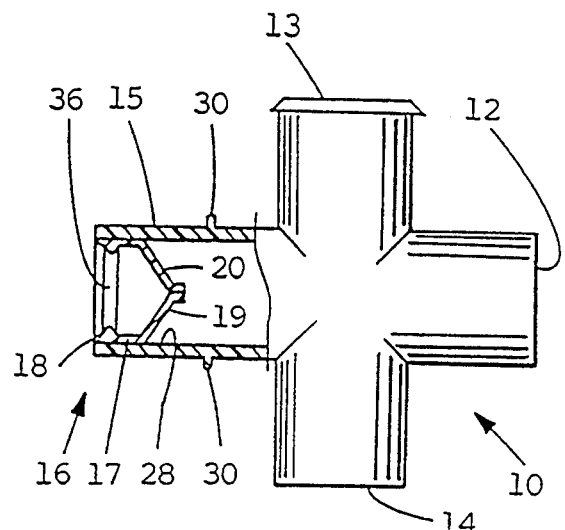
FIG. 2 shows a partial cutaway view of the respirator manifold, with the accessory device access port and a normally closed valve therein formed in accordance with the present invention being shown in cross-section.

Specifically, the manifold 10 of the present invention includes an accessory device access port 15 which is in fluid flow communication with the interior of the manifold 10 and the atmosphere. As best shown in FIG. 2, the access port 15 includes a normally closed valve 16 formed therein which maintains the interior of the manifold isolated from the atmosphere at all times.

As explained above, the interior of the manifold, although experiencing constant pressure fluctuations, is generally kept at a pressure which is slightly above atmospheric pressure in order to properly administer oxygen according to the PEEP procedure. Therefore, the valve 16 is preferably made of a resilient material. The base portion 17 of the valve 16 is formed to a generally cylindrical shape having an outer diameter equal to the inner diameter of the access port 15 and is fixed to the distal end 18 of the port 15 in a permanent, air-tight manner, such as by an adhesive or the like. The central portion 19 of the valve 16 is generally conical in shape. The top portion 20 of the valve 16 is normally constricted to a completely closed configuration which prevents passage of gases through the valve 16 under all normally occurring pressure differentials generated between the interior of the manifold 10 and the atmosphere during respiratory support of a patient.

As can be seen by the design of the valve 16, the central portion 19 and the top portion 20 thereof are designed so that they are assisted in remaining in their normally closed position whenever pressure within the manifold 10 is greater than atmospheric pressure. The constant excess pressure within the manifold 10 in a PEEP procedure, pushes against the central section 19 of the valve 16, and tends to force further collapse and closure of the valve 16 instead of forcing the valve 16 open.

If desired, a second sealing surface 36 which can complement the top portion 20 for sealing against the male adaptor 11 may also be included in the valve 16. Further sealing surfaces may also be included within valve 16 if desired.

Figure 3:
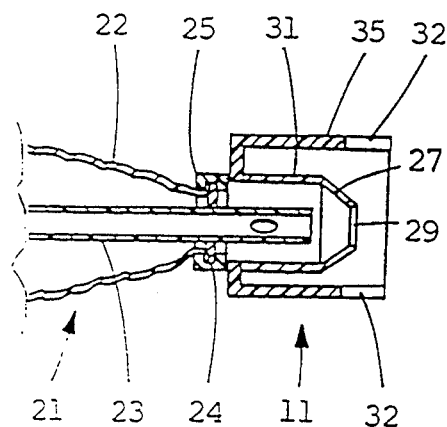
FIG. 3 is a cross-sectional view of a portion of an accessory device which includes the male adaptor formed in accordance with the principles of the present invention.

In FIG. 3, a cross-sectional view of the male adaptor 11 of the present invention as attached to an accessory device is shown. The accessory device (shown only in part) in the preferred embodiment of the invention is a suction catheter system. Therein, the male adaptor 11 of the present invention is permanently attached to the distal end of a sheath 22 which is designed to isolate the suction catheter 23 from the atmosphere. Further, in this embodiment, the male adaptor 11 also preferably includes a sealing ring 24 formed in the base 25 thereof through which the suction catheter 23 must pass in order to pass through the adaptor 11 and into the manifold 10 during use. The seal ring 24 is designed to allow movement of the suction catheter 23 therethrough while at the same time maintain a seal thereabout.

Figure 4:
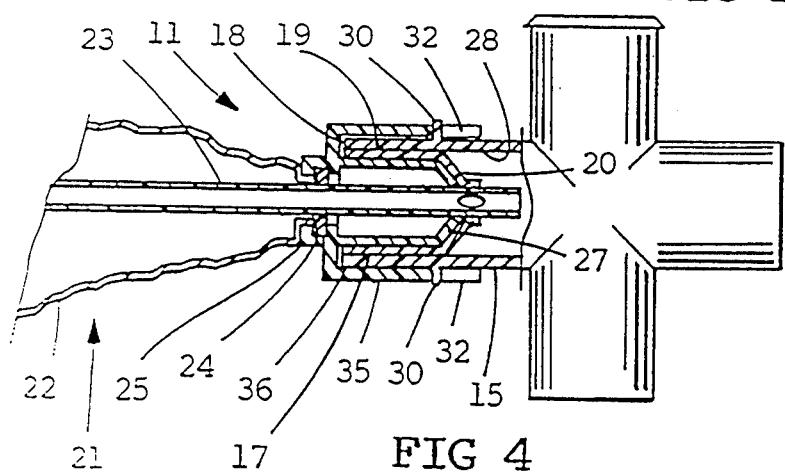
FIG. 4 is a partial cutaway view of the manifold and male adaptor as shown in FIG. 1, with the accessory device access port of the manifold and the male adaptor of the accessory device being shown in cross-section.

As best shown in FIG. 4, attachment of the male adaptor 11 to the respiratory manifold 10 is effected by insertion of the adaptor 11 into the opening 26 of the port 15 until the tapered top section 27 of the adaptor 11 engages the central portion 19 of the valve 16 and forces it toward the interior wall 28 of the port 15. Upon complete insertion of the adaptor 11 into the port 15, the central portion 19 of the valve 16 has been completely forced toward the interior wall 28, and the top portion 20 of the valve 16 has been stretched around the tapered top section 27 of the adaptor 11 to form an opening therethrough roughly equivalent to or greater in diameter than the top opening 29 of the adaptor 11.

As is readily evident, during insertion of the adaptor 11 into the access port 15, the sealing relationship formed between the valve 16 and the adaptor 11 during the initial phase of insertion, prior to opening of the top portion 20 of the valve 16, is intended to completely isolate the interior of the manifold 10 from the atmosphere during attachment of the accessory device. Once completely inserted within the port 15, the tapered top section 27 and the outer surface of the cylindrical central section 31 of the adaptor 11 are engaged in sealing relationship with the top portion 20 and central portion 19 respectively of the valve 16.

If desired, the port 15 may include a pair of nubs 30 thereon at radially opposed positions which are sized to accept a pair of arcuate slots 32 located on an adaptor locking cylinder 35, in locking relationship to ensure that inadvertent detachment of the adaptor 11 from the manifold 10 cannot occur.

As shown in FIG. 5, an alternative embodiment of the adaptor 11 of the present invention may includes a fluid entry port 33 formed thereon which is normally closed in any well known manner such as by a diaphragm or cap 34. The fluid entry port can be used to inject fluid into the adaptor 11 to clean the suction catheter 23 and the sealing ring 24 of materials withdrawn by the catheter 23 from the patient's lungs during an aspiration procedure.

Figure 6:
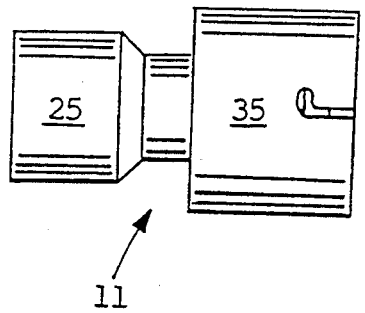
FIG. 6 is a partially cut away view of a third preferred embodiment of the male adaptor made in accordance with the principles of the present invention as adapted for use on other aspirator system accessory devices.

As shown in FIG. 6, a further alternative embodiment of the male adaptor 11 of the present invention may include various external diameters which will allow it to be attached to various other common respiratory system accessories such as a metered dose inhaler or a mechanical resuscitation bag.

It should be understood from the foregoing that, while particular embodiments of the invention have been illustrated and described, various modifications can be made thereto for its adaption to various accessory devices which can conceivably be used in conjunction with a respiratory system which require access to a patient's lungs while maintaining isolation of the respiratory system from the atmosphere. It is to be understood that adaption of the present invention for use on any such accessory device is well within the spirit and scope of the present invention.

When it is desired to remove the accessory device from the manifold 10, it is only necessary to unlock the nubs 30 of the adaptor 11 from the slots 32 of the port 15, and withdraw the adaptor 11 from the port opening 26. Due to the resilient nature of the valve 16, withdrawal of the adaptor 11 allows it to return to its normally closed position without exposure of the interior of the manifold 10 to the atmosphere. In this manner, accessory devices may attached and detached periodically to the manifold 10 without interruption of continuous respiratory support of a patient by the respiratory system and without loss of isolation of the respiratory system from the atmosphere. Although particular embodiments of the invention have been shown, it is not intended that the invention be limited thereby, instead, the scope of the present invention is intended to be limited only by the appended claims.

We claim:

1. A respiration system for use with respiration system accessories, comprising:
   a manifold for connecting a patient to a ventilator circuit said manifold including an accessory access port,
   an adaptor for attachment to said manifold, said adaptor being formed of a generally hollow tubular member having a proximal end and a distal end, said distal end including a cylindrical central section sized to be received within said accessory port, and
   said accessory access port allowing attachment of said adaptor to said manifold, said accessory access port including a normally closed valve formed of a soft elastomeric material which is closed to fluid flow through said accessory access port when said adaptor is not present therein, said adaptor having means for forcing said valve to an open position to allow fluid flow through said accessory access port responsive to said cylindrical central section of said adaptor being positioned completely within said accessory access port, said valve completely surrounding any portion of said cylindrical central section of said adaptor in a sealing manner to seal against fluid flow between said accessory access port and the outside of said cylindrical central section whenever any portion of said cylindrical central section is positioned within said accessory access port.

2. A respiration system according to claim 1 wherein said cylindrical central section includes a semi-conically shaped surface located at a distal end of said cylindrical central section.

3. A respiration system according to claim 1 wherein the respiration system accessory attached to said adaptor is a metered dose inhaler.

4. A respiration system according to claim 1 wherein the respiration system accessory attached to said adaptor is a mechanical resuscitation bag.

5. A respiration system according to claim 1 wherein said adaptor further includes a fluid inlet port adjacent said proximal end thereof.

6. A respiration system according to claim 1 further including means for locking said adaptor to said manifold when said adaptor is properly attached to said accessory access port.

7. A respiration system according to claim 1 wherein said normally closed valve is a one-way check valve.

8. A respiration system according to claim 1 wherein said adaptor further includes an annular restriction member positioned within said generally hollow tubular member for sealing against a portion of the respiration system accessory when positioned in said adaptor, whereby fluid flow between said generally hollow tubular member and the respiration system accessory is prevented.

9. A respiration system according to claim 8 wherein the respiration system accessory is a suction catheter system, and the portion of the respiration system accessory sealing against said annular restriction member includes a portion of a suction catheter.

* * * * *